(12) United States Patent
Eaton

(10) Patent No.: US 11,663,888 B2
(45) Date of Patent: *May 30, 2023

(54) HOME SECURITY RESPONSE USING BIOMETRIC AND ENVIRONMENTAL OBSERVATIONS

(71) Applicant: DISH Ukraine L.L.C., Kharkov (UA)

(72) Inventor: Zane Eaton, Kharkov (UA)

(73) Assignee: DISH UKRAINE L.L.C., Kharkov (UA)

( * ) Notice: Subject to any disclaimer, the term of this patent is extended or adjusted under 35 U.S.C. 154(b) by 0 days.

This patent is subject to a terminal disclaimer.

(21) Appl. No.: 17/245,311

(22) Filed: Apr. 30, 2021

(65) Prior Publication Data

US 2021/0247173 A1    Aug. 12, 2021

Related U.S. Application Data

(63) Continuation of application No. 16/714,330, filed on Dec. 13, 2019, now Pat. No. 11,022,422, which is a
(Continued)

(51) Int. Cl.
| | |
|---|---|
| G06F 9/54 | (2006.01) |
| G08B 5/22 | (2006.01) |
| G08B 15/00 | (2006.01) |
| G08B 21/04 | (2006.01) |
| G08B 29/18 | (2006.01) |
| G01B 3/00 | (2006.01) |
| G01B 5/012 | (2006.01) |
| G01B 7/012 | (2006.01) |

(Continued)

(52) U.S. Cl.
CPC ............. *G08B 5/223* (2013.01); *A61B 5/024* (2013.01); *G01B 3/008* (2013.01); *G01B 5/012* (2013.01); *G01B 7/012* (2013.01); *G01B 11/007* (2013.01); *G08B 1/08* (2013.01); *G08B 3/10* (2013.01); *G08B 5/36* (2013.01); *G08B 15/002* (2013.01); *G08B 21/0297* (2013.01); *G08B 21/0453* (2013.01); *G08B 25/14* (2013.01); *G08B 29/188* (2013.01); *H04L 12/2803* (2013.01)

(58) Field of Classification Search
CPC ..... G06F 9/542; G08B 29/185; G08B 29/188; G08B 31/00
USPC ........................................................ 719/318
See application file for complete search history.

(56) References Cited

U.S. PATENT DOCUMENTS

| | | |
|---|---|---|
| 8,171,148 B2 | 5/2012 | Lucas et al. |
| 9,015,225 B2 | 4/2015 | Paul et al. |

(Continued)

FOREIGN PATENT DOCUMENTS

| | | |
|---|---|---|
| WO | 2016/167736 A1 | 10/2016 |

OTHER PUBLICATIONS

International Search Report and Written Opinion for PCT/UA2015/000035 dated Jan. 14, 2016, all pages.

*Primary Examiner* — Andy Ho

(74) *Attorney, Agent, or Firm* — Kilpatrick Townsend & Stockton

(57) ABSTRACT

Various arrangements for handling a potential security situation using a home automation system are presented. A biometric measurement of a user may be received. An alert from a home automation device in wireless communication with the home automation host system may be received. If the biometric measurement is associated with the alert, a security response action may be performed.

20 Claims, 7 Drawing Sheets

Related U.S. Application Data continuation of application No. 15/566,377, filed as application No. PCT/UA2015/000035 on Apr. 17, 2015, now Pat. No. 10,580,265.

(51) Int. Cl.
| | |
|---|---|
| *G01B 11/00* | (2006.01) |
| *A61B 5/024* | (2006.01) |
| *G08B 1/08* | (2006.01) |
| *G08B 3/10* | (2006.01) |
| *G08B 5/36* | (2006.01) |
| *G08B 21/02* | (2006.01) |
| *G08B 25/14* | (2006.01) |
| *H04L 12/28* | (2006.01) |

(56) References Cited

U.S. PATENT DOCUMENTS

| | | |
|---|---|---|
| 9,178,923 B2 | 11/2015 | Paul et al. |
| 9,786,158 B2 | 10/2017 | Beaver |
| 10,580,265 B2 | 3/2020 | Eaton |
| 11,022,422 B2 | 6/2021 | Eaton |
| 2013/0088352 A1* | 4/2013 | Amis ............... G08B 15/002 340/540 |
| 2013/0201316 A1 | 8/2013 | Binder et al. |
| 2014/0368643 A1* | 12/2014 | Siegel ............. G08B 13/19695 348/143 |
| 2016/0234034 A1 | 8/2016 | Mahar et al. |

\* cited by examiner

HOME SECURITY RESPONSE USING BIOMETRIC AND ENVIRONMENTAL OBSERVATIONS

CROSS-REFERENCE TO RELATED APPLICATIONS

This application is a continuation of U.S. patent application Ser. No. 16/714,330, filed on Dec. 13, 2019, entitled "HOME SECURITY RESPONSE USING BIOMETRIC AND ENVIRONMENTAL OBSERVATIONS," which application is a continuation of U.S. patent application Ser. No. 15/566,377, filed on Oct. 13, 2017, entitled "HOME SECURITY RESPONSE USING BIOMETRIC AND ENVIRONMENTAL OBSERVATIONS," now U.S. Pat. No. 10,580,265, issued Mar. 3, 2020, which application is a U.S. National Stage of PCT International Application No. PCT/UA2015/000035, filed on Apr. 17, 2015, entitled "HOME SECURITY RESPONSE USING BIOMETRIC AND ENVIRONMENTAL OBSERVATIONS," the disclosures of which are hereby incorporated by reference in their entirety for all purposes.

BACKGROUND

Detecting home invasions, robberies, vandalism, burglaries, trespassing, and/or other security situations is typically performed using security devices such as cameras, microphones, motion detectors, and alarm systems. Solely relying on such devices can result in a significant number of false alarms, possibly resulting in wasted time and/or resources in responding to the false alarms. Worse still, if a high number of false alarms occur, alarms may start to be ignored, effectively eliminating the security present at a structure. For instance, animal activity near a structure can trigger motion detectors or a door left ajar can trigger an alarm system. Before taking action in response to a possible security situation, it may be useful to determine with a high level of probability that an actual security situation is present.

SUMMARY

Various systems, methods, devices, and computer-readable mediums are presented for handling a potential security situation. In some embodiments, during a defined active monitoring time period, a biometric measurement of a user may be received, the biometric measurement of the user exceeding a defined threshold value for the biometric measurement, wherein the biometric measurement of the user is associated with a first time. A security alert from a home automation device in wireless communication with the home automation host system may be received, wherein the security alert is associated with a second time. The first time associated with the biometric measurement may be determined to be within a threshold time period of the second time associated with the security alert received from the home automation device. In response to determining the first time associated with the biometric measurement is within the threshold time period of the second time associated with the security alert received from the home automation device, a security response action may be performed.

Embodiments of such a system, method, device or computer-readable medium may include one or more of the following features: The security response action may include the home automation host system transmitting a message that causes a light to be illuminated, wherein the light serves as illumination for a room within a structure in which the home automation system is installed. The security response action may include presenting, via a display device, a video feed from a camera that captures video corresponding to a location of the security alert. The security response action may include contacting an emergency service. The security response action may include activating a television receiver and a sound system that receives audio data from the television receiver and transmitting, to the television receiver, an instruction to output sound by outputting at least one sound source selected from the group consisting of: a recorded television program, a recorded sound, and a live broadcast of a television channel. The security response may include transmitting, to the television receiver, by the home automation host system, a second instruction to set a defined volume level for outputting sound via the sound system. The biometric measurement may be a heart rate and the defined threshold value is based on a measured resting heart rate of the user. In some embodiments, a questionnaire is output via a presentation device, wherein the questionnaire presents an option to the user as to how the home automation host system should respond to the security alert if the biometric measurement of the user exceeds the defined threshold value for the biometric measurement. In some embodiments, a message may be caused to be sent to a defined external contact, the defined external contact having been previously defined by the user.

BRIEF DESCRIPTION OF THE DRAWINGS

A further understanding of the nature and advantages of various embodiments may be realized by reference to the following figures. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

Figure 1:
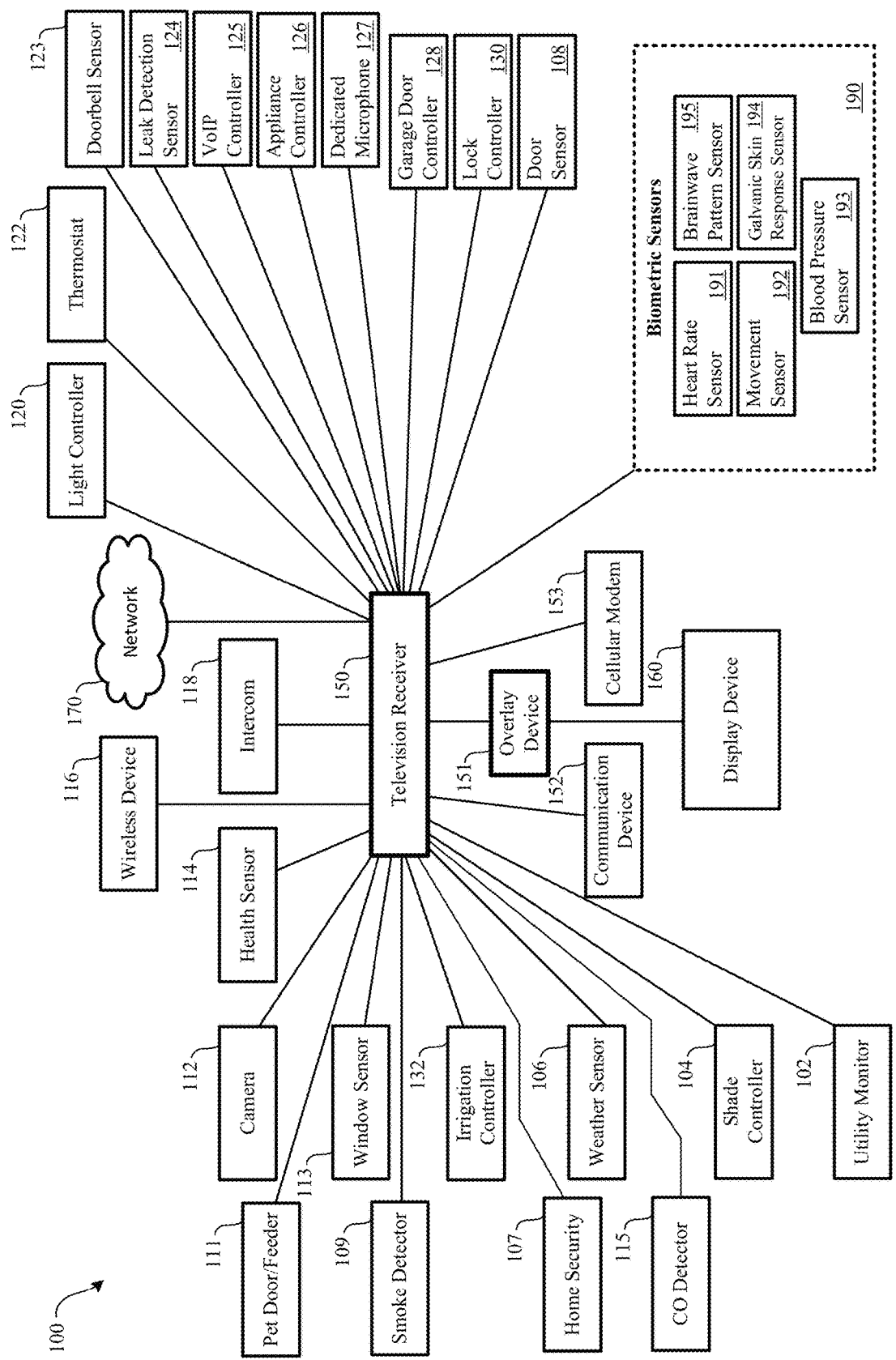
FIG. 1 illustrates an embodiment of a home automation system.

Information gathered by security-related devices in a home automation system can be used in conjunction with information gathered from one or more biometric sensors that are monitoring a user to determine if a break-in or other security threat is present. Individually, information from security-related devices may be subject to occasional false alarm, such as by an animal triggering a motion sensor. Similarly, biometric information, such as heart rate, blood pressure, and brainwave patterns may move in accordance with a user's dream pattern when asleep. However, if a security-related device detects a potential threat (e.g., by sound) and the user's biometric readings are elevated, there is a likelihood that these measurements are correlated and are resulting from the same triggering event.

When a biometric reading exceeds a threshold level (referred to as a biometric alert) and a security threat (referred to as a security alert) has been detected by a home automation system, the home automation system may perform one or more response actions. The one or more responses taken can vary based on the user's preference. For instance, response actions can include: outputting sounds (e.g., by turning on a television, outputting content and turning the volume up), outputting and/or recording security camera footage (e.g., camera footage from the vicinity of where the security alert was determined to occur may be recorded and/or output to a presentation device by the home automation host system), contacting one or more emergency services (e.g., police, fire, ambulance, security guard, private security company, etc.), contacting one or more private contacts (e.g., a neighbor, a relative), turning on one or more lights (which serve as illumination for a room), locking one or more doors, shutting off lights (as opposed to turning them on), responding to user voice commands to take requested actions (e.g., "turn on all lights", "turn on all televisions"), flushing one or more toilets (e.g., to generate sound), turning on the hot tub (e.g., to generate sound), and/or turning on the sprinklers (e.g., sound, and to mark any criminal on property by making him wet). Other response actions are also possible.

In some embodiments, a response can be performed by the home automation system in response to just biometric information gathered from a user. If it is determined that the user is awake, the current time is within a certain time period (e.g., between 1 AM-4 AM), and the user's biometric readings are elevated (a biometric alert is detected), one or more of the previously detailed response actions may be taken by the home automation host system. Whether a security-device has detected a potential security threat within a threshold amount of time of the user's elevated biometric information may affect the type of response that the home automation system performs. For instance, if only elevated biometric information triggers the response, a minor response may be performed, such as turning on one or more lights (that serve as illumination for a room or outdoor area). But, if elevated biometric information is received within a threshold time of a security threat being detected by one or more home automation security devices, a more major response may be made, such as: turn one or more lights on, output sound, and contact a security guard. The specific response may be determined based on a questionnaire that the user previously answered that defines how the home automation system will respond to particular situations.

FIG. 1 illustrates an embodiment of a home automation system. A home automation system that includes multiple home automation devices and a home automation host may be used in measuring biometric measurements of a user and obtaining security information in and around a structure (e.g., home, building, office, warehouse, etc.). FIG. 1 illustrates an embodiment of a home automation system 100 hosted by a television receiver (that serves at the home automation host system). Television receiver 150 may be configured to receive television programming from a satellite-based television service provider; in other embodiments, other forms of television service provider networks may be used, such as an IP-based network (e.g., fiber network), a cable based network, a wireless broadcast-based network, etc.

Television receiver 150 may be configured to communicate with various home automation devices. The devices with which television receiver 150 communicates may use different communication standards. For instance, one or more devices may use a ZigBee® communication protocol while one or more other devices communicate with the television receiver using a Z-Wave® communication protocol. Other forms of wireless communication may be used by devices and the television receiver. For instance, television receiver 150 and one or more devices may be configured to communicate using a wireless local area network, which may use a communication protocol such as IEEE 802.11.

In some embodiments, a separate device may be connected with television receiver 150 to enable communication with home automation devices. For instance, communication device 152 may be attached to television receiver 150. Communication device 152 may be in the form of a dongle. Communication device 152 may be configured to allow for Zigbee®, Z-Wave®, and/or other forms of wireless communication. The communication device may connect with television receiver 150 via a USB port or via some other type of (wired) communication port. Communication device 152 may be powered by the television receiver or may be separately coupled with a power source. In some embodiments, television receiver 150 may be enabled to communicate with a local wireless network and may use communication device 152 in order to communicate with devices that use a ZigBee® communication protocol, Z-Wave® communication protocol, and/or some other home wireless communication protocols.

Communication device 152 may also serve to allow additional components to be connected with television receiver 150. For instance, communication device 152 may include additional audio/video inputs (e.g., HDMI), a component, and/or a composite input to allow for additional devices (e.g., Blu-ray players) to be connected with television receiver 150. Such connection may allow video from such additional devices to be overlaid with home automation information. Whether home automation information is overlaid onto video may be triggered based on a user's press of a remote control button.

Regardless of whether television receiver 150 uses communication device 152 to communicate with home automation devices, television receiver 150 may be configured to output home automation information for presentation to a user via display device 160, which may be a television, monitor, or other form of device capable of presenting visual information. Such information may be presented simultaneously with television programming received by television receiver 150. Television receiver 150 may also, at a given time, output only television programming or only home automation information based on a user's preference. The user may be able to provide input to television receiver 150 to control the home automation system hosted by television receiver 150 or by overlay device 151, as detailed below.

In some embodiments, television receiver 150 may not be used as a host for a home automation system. Rather, a separate device may be coupled with television receiver 150 that allows for home automation information to be presented to a user via display device 160. This separate device may be coupled with television receiver 150. In some embodiments, the separate device is referred to as overlay device 151. Overlay device 151 may serve as the home automation host system and may be configured to overlay (or separately output) information, such as home automation information, onto a signal to be visually presented via display device 160, such as a television. In some embodiments, overlay device 151 may be coupled between television receiver 150, which may be in the form of a set top box (STB), and display device 160, which may be a television, monitor, or other form of presentation device. In such embodiments, television receiver 150 may receive, decode, descramble, decrypt, store, and/or output television programming. Television receiver 150 may output a signal, such as in the form of an HDMI signal. Rather than be directly input to display device 160, the output of television receiver 150 may be input to overlay device 151. Overlay device 151 may receive the video and/or audio output from television receiver 150. Overlay device 151 may add additional information to the video and/or audio signal received from television receiver 150. The modified video and/or audio signal may be output to display device 160 for presentation. In some embodiments, overlay device 151 has an HDMI input and an HDMI output, with the HDMI output being connected to display device 160. To be clear, while FIG. 1 illustrates lines illustrating communication between television receiver 150 and various devices, it should be understood that such communication may exist, in addition or alternatively via communication device 152 and/or with overlay device 151. It should be understood that all of the home automation functions attributed to a home automation host in this document can be performed by television receiver 150 (if enabled for home automation) or by overlay device 151.

In some embodiments, television receiver 150 may be used to provide home automation functionality but overlay device 151 may be used to present information via display device 160. It should be understood that the home automation functionality detailed herein in relation to a television receiver may alternatively be provided via overlay device 151. In some embodiments, overlay device 151 may provide home automation functionality and be used to present information via display device 160. Using overlay device 151 to present automation information via display device 160 may have additional benefits. For instance, multiple devices may provide input video to overlay device 151. For instance, television receiver 150 may provide television programming to overlay device 151, a DVD/Blu-Ray player may provide video overlay device 151, and a separate internet-TV device may stream other programming to overlay device 151. Regardless of the source of the video/audio, overlay device 151 may output video and/or audio that has been modified to include home automation information and output to display device 160. As such, in such embodiments, regardless of the source of video/audio, overlay device 151 may modify the audio/video to include home automation information and, possibly, solicit for user input. For instance, in some embodiments, overlay device 151 may have four video inputs (e.g., four HDMI inputs) and a single video output (e.g., an HDMI output). In other embodiments, such overlay functionality may be part of television receiver 150. As such, a separate device, such as a Blu-ray player, may be connected with a video input of television receiver 150, thus allowing television receiver 150 to overlay home automation information when content from the Blu-Ray player is being output to display device 160.

Regardless of whether television receiver 150 is itself configured to provide home automation functionality and output home automation input for display via display device 160 or such home automation functionality is provided via overlay device 151, home automation information may be presented by display device 160 while television programming is also being presented by display device 160. For instance, home automation information may be overlaid or may replace a portion of television programming (e.g., broadcast content, stored content, on-demand content, etc.) presented via display device 160.

Television receiver 150 or overlay device 151 may be configured to communicate with one or more wireless devices, such as wireless device 116. Wireless device 116 may represent a tablet computer, cellular phone, laptop computer, remote computer, or some other device through which a user may desire to control home automation settings and view home automation information. Such a device also need not be wireless, such as a desktop computer. Television receiver 150, communication device 152, or overlay device 151 may communicate directly with wireless device 116, or may use a local wireless network, such as network 170. Wireless device 116 may be remotely located and not connected with a same local wireless network. Via the Internet, television receiver 150 or overlay device 151 may be configured to transmit a notification to wireless device 116 regarding home automation information. For instance, in some embodiments, a third-party notification server system, such as the notification server system operated by Apple®, may be used to send such notifications to wireless device 116.

In some embodiments, a location of wireless device 116 may be monitored. For instance, if wireless device 116 is a cellular phone, when its position indicates it has neared a door, the door may be unlocked. When bedside (e.g., within a threshold distance) it may be assumed that the user is in bed. Such a determination may also require a certain time of day, such as between 10 PM and 5 AM. A user may be able to define which home automation functions are controlled based on a position of wireless device 116. Other functions could include opening and/or closing a garage door, adjusting temperature settings, turning on and/or off lights, opening and/or closing shades, etc. Such location-based control may also take into account the detection of motion via one or more motion sensors that are integrated into other home automation devices and/or stand-alone motion sensors in communication with television receiver 150.

In some embodiments, little to no setup of network 170 may be necessary to permit television receiver 150 (or overlay device 151) to stream data out to the Internet. For instance, television receiver 150 and network 170 may be configured, via a service such as Sling® or other video streaming service, to allow for video to be streamed from television receiver 150 to devices accessible via the Internet. Such streaming capabilities may be "piggybacked" to allow for home automation data to be streamed to devices accessible via the Internet. For example, U.S. patent application Ser. No. 12/645,870, filed on Dec. 23, 2009, entitled "Systems and Methods for Remotely Controlling a Media Server via a Network", which is hereby incorporated by reference, describes one such system for allowing remote access and control of a local device. U.S. Pat. No. 8,171,148, filed Apr. 17, 2009, entitled "Systems and Methods for Establishing Connections Between Devices Communicating Over a Network", which is hereby incorporated by reference, describes a system for establishing connection between devices over a network. U.S. patent application Ser. No. 12/619,192, filed May 19, 2011, entitled "Systems and Methods for Delivering Messages Over a Network", which is hereby incorporated by reference, describes a message server that provides messages to clients located behind a firewall.

Wireless device 116 may serve as an input device for television receiver 150. For instance, wireless device 116 may be a tablet computer that allows text to be typed by a user and provided to television receiver 150. Such an arrangement may be useful for text messaging, group chat sessions, or any other form of text-based communication. Other types of input may be received for the television receiver from a tablet computer or other device as shown in the attached screenshots, such as lighting commands, security alarm settings and door lock commands. While wireless device 116 may be used as the input device for typing text, television receiver 150 may output for display text to display device 160.

In some embodiments, a cellular modem 153 may be connected with either overlay device 151 or television receiver 150. Cellular modem 153 may be useful if a local wireless network is not available. For instance, cellular modem 153 may permit access to the Internet and/or communication with a television service provider. Communication with a television service provider may also occur via a local wireless or wired network connected with the Internet. In some embodiments, information for home automation purposes may be transmitted by a television service provider system to television receiver 150 or overlay device 151 via the television service provider's distribution network, which may include the use of satellites.

Various home automation devices may be in communication with television receiver 150 or overlay device 151. Such home automation devices may use disparate communication protocols. Such home automation devices may communicate with television receiver 150 directly or via communication device 152. Such home automation devices may be controlled by a user and/or have a status viewed by a user via display device 160 and/or wireless device 116. Further, at least some of such home automation devices may be security-related uses—such as monitoring for intruders. Home automation devices may include: door sensor 108, lock controller 130 (which may be integrated with door sensor 108), smoke detector 109, carbon monoxide detector 115, home security system 107, pet door/feeder 111, camera 112, window sensor 113, irrigation controller 132, weather sensor 106, shade controller 104, utility monitor 102, heath sensor 114, intercom 118, light controller 120, thermostat 122, leak detection sensor 124, appliance controller 126, garage door controller 128, doorbell sensor 123, and VoIP controller 125.

At least some of these home automation devices may be used to monitor the security of the structure in which they are installed. Relevant data transmitted to the home automation host system may serve as a security alert (that is, information that is relevant to security of the structure). Security alerts may be gleaned from: door sensor 108, which may be used to determine when a door has been opened; lock controller 130, which may be used to determine when a lock has been unlocked; smoke detector 109, which may be used to determine when smoke is present; carbon monoxide detector 115, which may be used to determine when carbon monoxide is present; home security system 107, which may include one or more window monitors, door monitors, motion sensors, microphones, and/or cameras that are used to monitor for an intrusion, motion, and/or sound; pet door/feeder 111, which may monitor for the pet door being opened; camera 112, which may monitor for motion or a person; window sensor 113, which may be used to determine if the window is opened; intercom 118 and/or dedicated microphone 127, which may be used to monitor for sounds through the structure; garage door controller 128, which may be used to determine if a garage door is opened; and doorbell sensor 123, which may be used to determine if the doorbell is actuated. Other security related sensors also may be possible. All of the above information may be relevant to security, especially if received during a time when the user is typically sleeping, such as a user defined time period of 10 PM-5 AM; or a time when the user is determined to be sleeping (e.g., based on his location, the location of his mobile device, the state of lights within the structure and/or the room he is within, the user being determined to be in bed with the lights off, etc.).

Additional forms of sensors not illustrated in FIG. 1 may also be incorporated as part of a home automation system. For instance, a mailbox sensor may be attached to a mailbox to determine when mail is present and/or has been picked up. The ability to control one or more showers, baths, and/or faucets from television receiver 150, overlay device 151 and/or wireless device 116 may also be possible. Pool and/or hot tub monitors may be incorporated into a home automation system. Such sensors may detect whether or not a pump is running, water temperature, pH level, a splash/whether something has fallen in, etc. Further, various characteristics of the pool and/or hot tub may be controlled via the home automation system. In some embodiments, a vehicle dashcam may upload or otherwise make video/audio available to television receiver 150 (or overlay device 151) when within range. For instance, when a vehicle has been parked within range of a local wireless network with which television receiver 150 is connected, video and/or audio may be transmitted from the dashcam to the television receiver for storage and/or uploading to a remote server.

Various biometric sensors 190 may be used to monitor a user. Such biometric sensors may be present on the user (e.g., by the user wearing a watch, pendant, bracelet, or other device that has one or more biometric sensors on-board) or by such biometric sensors being installed in the vicinity of where the user will be present when the biometric readings of the user are desired to be monitored. For instance, some of biometric sensors 190 may be mounted in the vicinity of the user's bed. Heart rate sensor 191 may monitor the user's heart rate. Movement sensor 192 may monitor whether the user is moving (e.g., tossing and turning in bed). Blood pressure sensor 193 may monitor the user's blood pressure. Brainwave pattern sensor 195 may monitor an activity level of the user's brain (e.g., to identify sleep, REM sleep, being awake, etc.). Galvanic skin response sensor 194 may monitor the user's skin for sweat/dampness, which can be indicative of the user's emotional state (e.g., nervousness, scared, calm, etc.). Other types of biometric sensors are also possible. Such biometric sensors 190 may communicate, such as wirelessly, with the device serving as the home automation host system (e.g., television receiver 150 or overlay device 151) either directly or indirectly.

Figure 2:
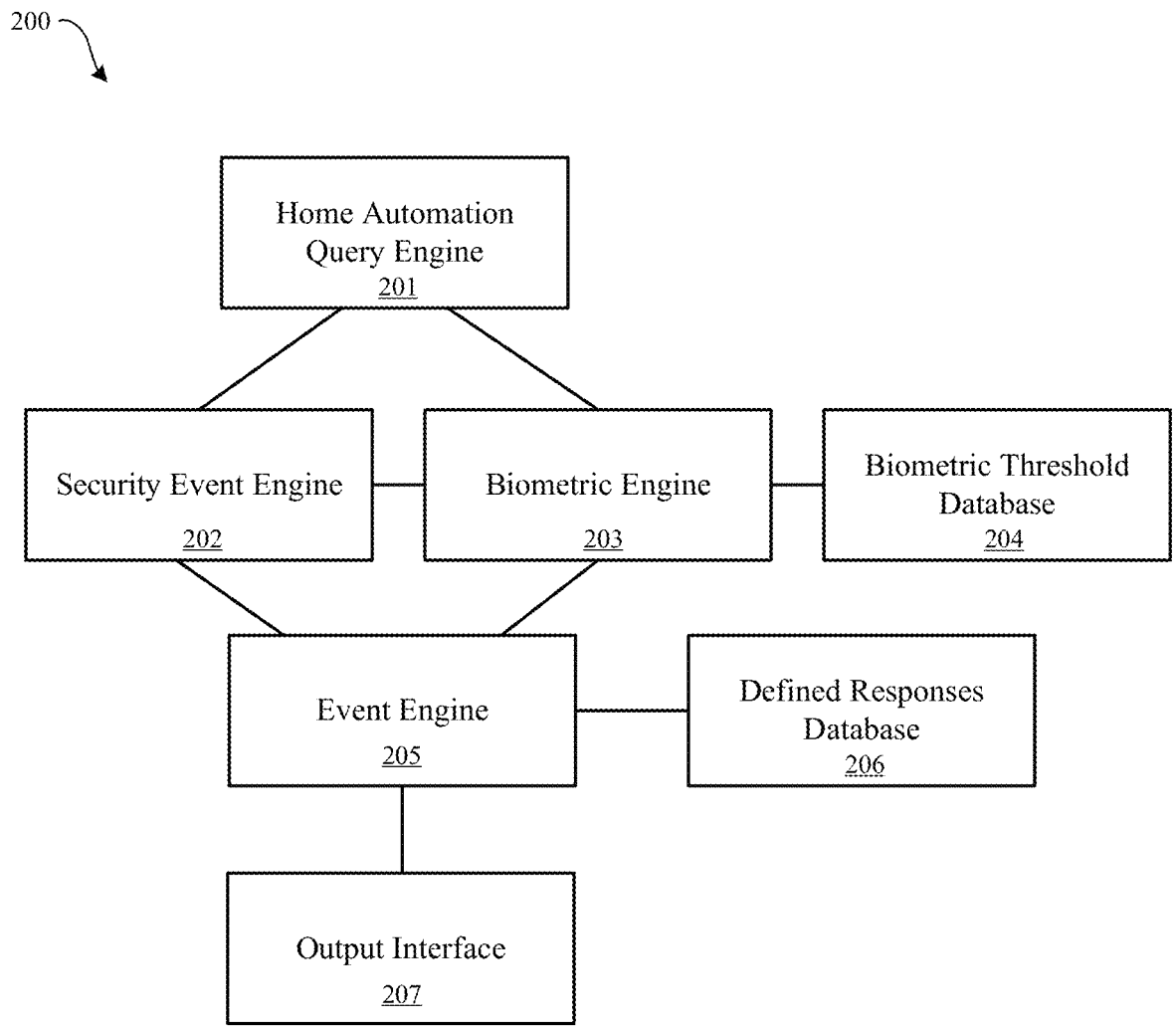
FIG. 2 illustrates an embodiment of components of a home automation host system that can perform various actions in response to an identified security situation.

FIG. 2 illustrates an embodiment 200 of components of a home automation host system that can perform various actions in response to an identified security situation. Such components may be incorporated as part of a television receiver, overlay device, or some other form of device that functions as a home automation host system. The home automation host system may include: home automation query engine 201, security event engine 202, biometric engine 203, biometric threshold database 204, event engine 205, defined responses database 206, and output interface 207. The components of embodiment 200 may be implemented using specially-purposed hardware, firmware, and/or software executed by underlying hardware.

Home automation query engine 201 may serve to periodically query biometric devices and/or home automation devices related to security for status updates. Biometric devices may determine when an anomalous condition (a biometric alert) has occurred and may only respond to such queries when a measured biometric condition is above or below a threshold or outside a threshold range. In other embodiments, evaluation of the biometric condition is performed by biometric engine 203. In such embodiments, in response to a query, a biometric device may respond with one or more most-recent biometric measurements that have been measured. The home automation host system may then determine whether a biometric alert is present based on the one or more measurements and stored threshold or range data. Queries may be handled in a similar way for security-related home automation devices: security-related home automation devices may determine when an anomalous condition has occurred and may only respond to such queries when a captured security-related home automation condition is above or below a threshold or outside a threshold range. In some embodiments, rather than home automation query engine 201 querying biometric devices and/or security-related home automation devices, such devices may periodically transmit information indicative of biometric measurements and security conditions, respectively, to home automation query engine 201.

Security event engine 202 may analyze data received by home automation query engine 201 from various home automation security devices. Security event engine 202 may determine if a security alert is present. Such a determination may be paid based on the content of the data received by home automation query engine 201 or by comparing the received data to a threshold value or other form of stored value by security event engine 202. Similarly, biometric engine 203 may analyze data received by home automation query engine 201 from various biometric devices to determine if biometric alerts are present. Biometric engine 203 may determine if a biometric measurement of the user is elevated or otherwise outside of a normal range by comparing the biometric measurement to one or more stored values in biometric threshold database 204. Such stored values may be based on an average for a person of similar height, weight, age, and gender or may be specific to the user, such as by measuring the user's blood pressure or heart rate when the user is known to be at rest.

Security event engine 202 may transmit an indication of the security alert to event engine 205 when such a security alert is identified. Similarly, biometric engine 203 may transmit a biometric alert to event engine 205 when such a biometric alert is identified by biometric engine 203. Event engine 205 may analyze data received from both security event engine 202 and biometric engine 203. For instance, event engine 205 may determine when a security event and biometric event have happened within a defined time period of each other and, thus, are likely attributed to a same cause (e.g., a burglar breaking into the user's house). Depending on the particular biometric measurement which triggered the biometric alert and/or the particular type of security alert, event engine 205 may consult defined responses database 206 to look up an appropriate response to be output. Entries in defined responses database 206 may be defaults defined by a service provider and/or entries that are defined by the user when configuring the system.

Output interface 207 may receive an indication of a defined response to be output. Output interface 207 may cause the content of the defined response forwarded by event engine 205 to be implemented. For instance, this may include output interface 207 interfacing with one or more telecommunication networks and/or communicating with one or more home automation devices present within the structure (e.g., to turn on a light).

Figure 3:
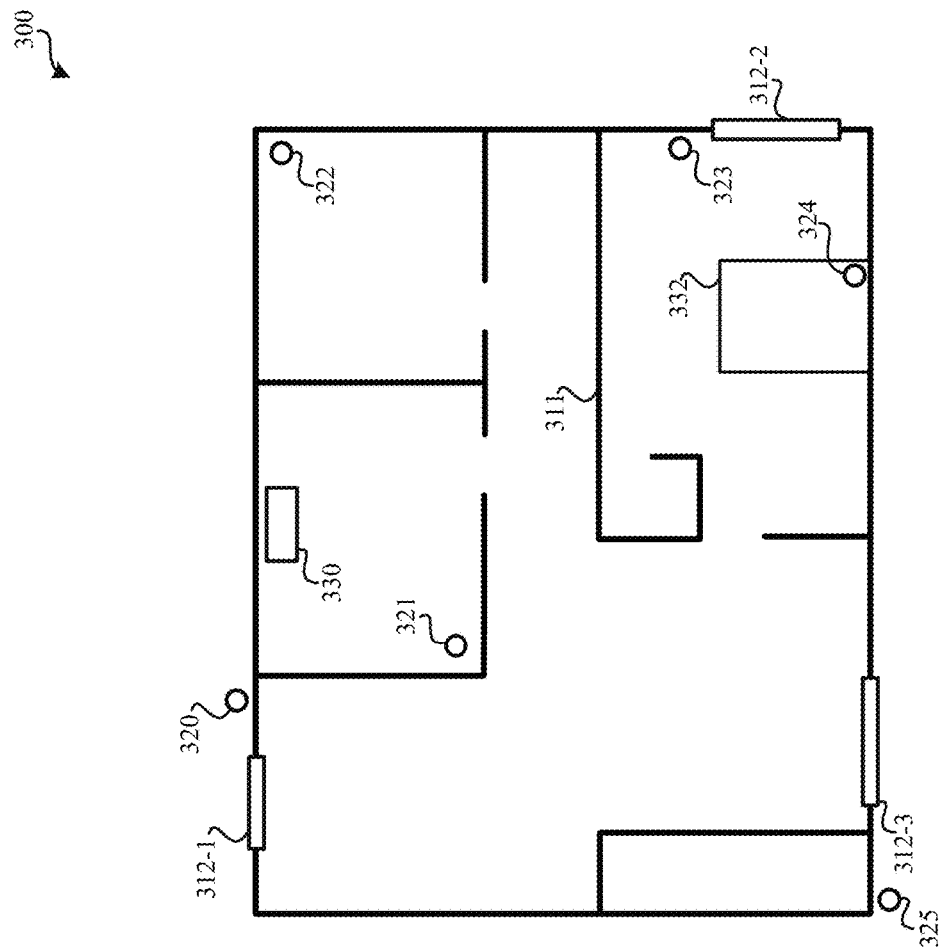
FIG. 3 illustrates an embodiment of a floor plan of a structure having an installed home automation system.

FIG. 3 illustrates an embodiment of a floor plan 300 of a structure having an installed home automation system. Present on floor plan 300 are doors 312 (312-1, 312-2, and 312-3), walls, such as wall 311 (only one wall labeled for simplicity), and bed 332. Also present are home automation devices 320, 321, 322, 323, and 325. Biometric device 324 may be either worn by user, attached to bed 332, or otherwise in the vicinity of bed 332 to monitor the user while he is asleep or attempting to sleep. As an example, home automation device 320 may be a motion detector. Information that can serve as security alert may be transmitted by home automation device 320 to home automation host system 330 when motion is detected. Such information may only be transmitted during particular times, such as during the night, when motion in the vicinity of door 312-1 is potentially suspicious. Home automation device 325 may be a camera (possibly with an on-board microphone). When video is captured that includes motion or sound above a certain threshold volume is detected, information that may serve as a security alert may be transmitted to home automation host system 330. Similar information that can serve as a security alert may be transmitted to home automation host system 330 by home automation device 322. Such home automation devices may be any of the security-related home automation devices detailed in relation to FIG. 1.

Biometric device 324 may also communicate with home automation host system 330. Biometric device 324 may be configured to only transmit information to home automation host system 330 when a user is either wearing biometric device 324, is in the vicinity of biometric device 324, or during a particular time of day such as when the user is expected to be asleep or trying to sleep. Home automation host system 330, which may be an overlay device or television receiver as detailed in relation to FIG. 1, may receive information from both home automation devices and biometric devices, such as biometric device 324 and may use such information to determine when a potential security situation is present. As an example, if home automation host system 330 determines that a security situation is present, based on information received from biometric device 324 and a home automation device, one action home automation host system 330 may take is to turn on a light, which may be home automation device 322.

Figure 4:
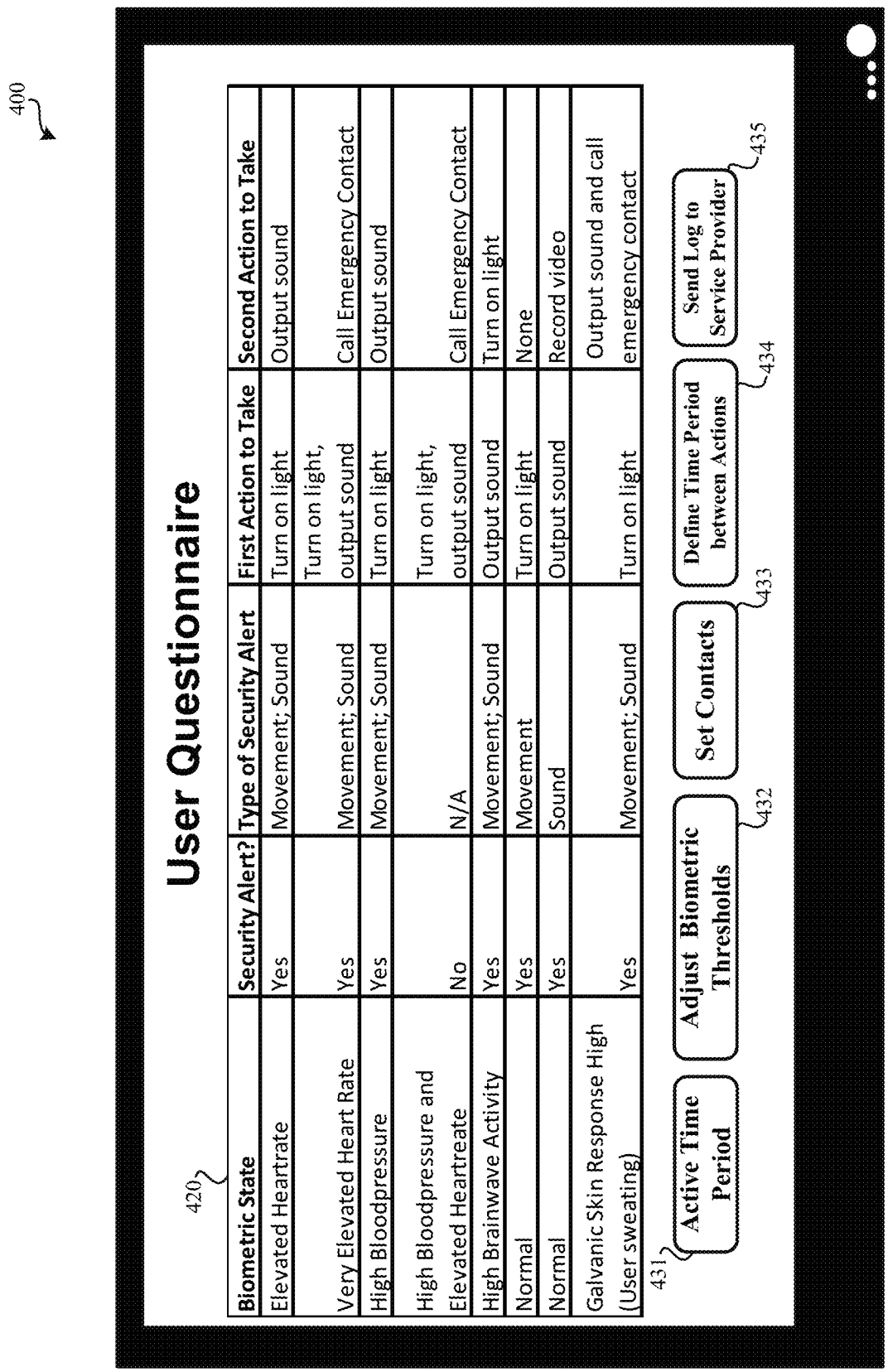
FIG. 4 illustrates an embodiment of a presentation device showing a questionnaire used to determine how the home automation host system should respond to various security situations.

FIG. 4 illustrates an embodiment of a display device 400 (which can represent display device 160 of FIG. 1) showing a questionnaire output by a home automation host system used to determine how the home automation host system should respond to various security situations. In the illustrated embodiment, in table 420 a user is presented with various biometric states that correspond to biometric devices that the user has configured to communicate with a home automation host system. In relation to the various biometric states, a user is presented with various indications of whether or not a security alert is present and the type of security alert. Similarly, the types of security alerts may correspond to types of security alerts that can be detected by home automation devices that the user has installed in his home and is configured to communicate with the home automation host system. The user can set a first action to take and, possibly, a follow-up, a second action to take after an amount of time (the amount of time is discussed in relation to option 434). In some embodiments, at least some of the defined actions may be set as a default by the service provider. The availability of actions may be based on the types of home automation devices that are in communication with the home automation host system. For instance, in table 420, a user may be presented with a drop-down menu or other form of selection to select among actions to take that are possible by the home automation devices that the user has installed and configured to communicate with the home automation host system. As an example, turning on a light may only be presented as an option if the user has installed a home automation enabled light. In some embodiments, turning on a presentation device and/or outputting sound via a sound system with a presentation device itself may always be an option if the home automation host system is part of a television receiver or is in communication with the television receiver.

While various combinations of biometric states (biometric alerts) are presented in combination with various types of security alerts, it should be understood that similar combinations may be presented in formats other than as presented in table 420. For instance, a user may be presented with a series of questions that can be used to gather similar information, such as "If your heartrate is elevated and movement is detected outside your home, what action would you like the home automation system to take?"

It could also be possible for the home automation host system to give a user recommendations on how to setup the system. For example, if the user's structure does not have a motion detector as part of his home automation system, the questionnaire interface could recommend that the user have one installed as a way to decrease a number of false alarms. As another example, the home automation host system could output for presentation statistics on home invasions and what the most common and/or effective way for configuring the home automation system to decrease such invasions. Such aspects could be beneficial for promoting sales of motion detectors and other home automation security devices.

Various options may be available to user to customize how security is handled at the user structure by the home automation host system. For instance, active time period option 431 allows the user to define when the monitoring of security and biometric alerts will occur. Typically, a user may only want such information monitored at night when the user is typically sleeping. Adjust biometric thresholds option 432 may be used to set or adjust the threshold used to determine when biometric measurements are outside of normal ranges. For instance, adjust biometric thresholds option 432 may be used to define a number of beats per minute (bpm), which, if the user's heart rate is above the defined bpm, indicates a biometric alert. Thresholds may be determined based on user-defined values or by performing measurements on the user while at rest and increasing the rest measurements by a defined delta value. For instance, if the user's resting heart rate is 65 bpm, a delta value of 25 bpm may be added to establish a threshold heart rate of 90 bpm for use in determining when a biometric alert is present.

The interface may allow the user to set differing responses for when a biometric alert is identified that is unaccompanied by a security alert (and the reverse situation). For instance, if the user's heartrate is determined to be elevated, a response such as turning on a light may be used but if accompanied by a security alert within a threshold time of the biometric alert, a stronger response, such as making noise, turning on a television, and turning on a light may be used.

Set contacts option 433 may allow a user to define one or more other persons who are contacted as part of either a first or second action in response to a biometric alert and/or security alert. The user may be permitted to specific a telephone number, email address, social media account, etc. that is contacted in response to a biometric alert and/or security alert combination, such as presented in table 420.

If the user has several people listed in his contacts for emergency contacts, geo-location of such individuals may be used to identify and closest contact. For example, if the user has three people listed, such as his father, brother and sister. His father lives closest, but is in New York for a business trip as identified using geo-location. His brother's phone is identified as in Florida, so the home automation host system would end up contacting the sister—who, despite being 40 miles away is still the closest contact.

Define time period between actions option 434 may allow the user to specify an amount of time that elapses between when a first action is taken and a second action is taken. This may allow a user time to disable the system from performing the second action if the user does not desire such an action to be taken (e.g., the user is aware that there is no security situation). The time period between actions may be defined to be times such as 20 seconds, 30 seconds, 1 minute, 5 minutes, etc.

Send log to service provider option 435 may allow information about biometric alerts and security alerts to be transmitted to a service provider. Such a service provider may store and/or analyze the received data for patterns and may compare such data with data collected from other users in the area.

Figure 5:
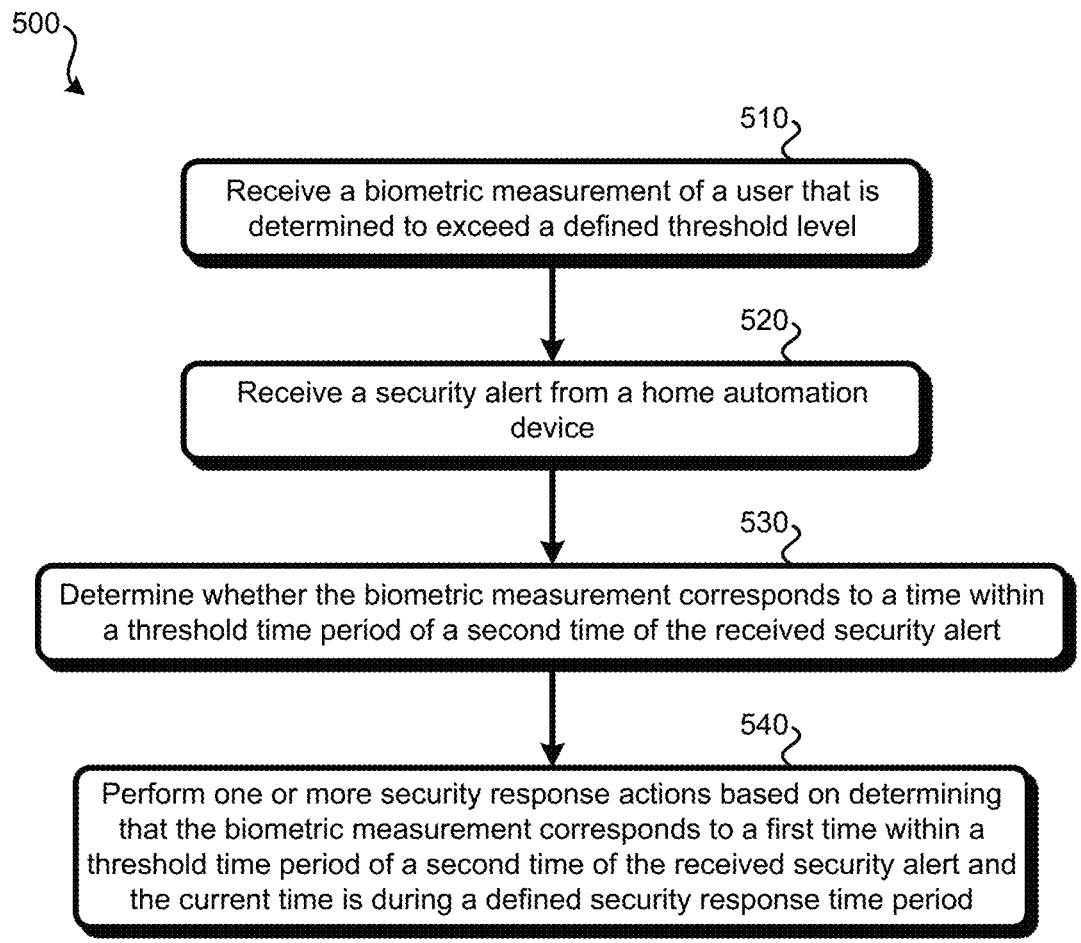
FIG. 5 illustrates an embodiment of a method for handling a potential security situation using a home automation system.

FIG. 5 illustrates an embodiment of a method 500 for handling a potential security situation using a home automation system. Method 500 may be performed using various home automation systems, such as the home automation systems detailed in relation to FIGS. 1-4. Each step of method 500 may be performed by the home automation host system.

At block 510, a biometric measurement of the user may be received by the home automation host system. The home automation host system may determine that the received biometric measurement exceeds a defined threshold level specific to that type of biometric measurement. In some embodiments, rather than the home automation host system performing a comparison between the biometric measurement and the defined threshold level, such an analysis may be performed by the biometric device itself. In such embodiments, the received biometric measurement may have been transmitted due to the biometric measurement having been determined to exceed the defined threshold level. As a simple example, a biometric measurement of the user's heart rate may be made and may have a value of 90 bpm. The value of 90 bpm may be determined to exceed the defined threshold value of 87 bpm. As such, the value of 90 bpm may be interpreted as being a biometric alert, that is a biometric measurement that exceeds a defined threshold level or is otherwise outside of a normal range.

At block 520, a security alert from a home automation device may be received by the home automation host system. In some embodiments, the data received from the home automation device is analyzed by the home automation host system to determine whether a security alert is present. In other embodiments, the home automation device itself analyzes the data and determines that a security alert is present and transmits indication of the security alert to the home automation host system.

At block 530, it is determined whether the biometric measurement of block 510 corresponds to a time within a defined threshold period of time of the security alert of block 520. Therefore, if the biometric measurement is received (or measured) at a first time and the security alert is received (or measured) at a second time, it is determined whether the first time is within a threshold time period of the second time. If it is not, it may be assumed that the biometric measurement of block 510 is unrelated to the security alert of block 520. If the first and second times are within a threshold time period of each other, it may be determined that the biometric measurement of block 510 is related to the security alert of block 520. As a simple example, the threshold time period may be 20 seconds; of course, threshold time periods that are of shorter duration or longer duration are also possible.

At block 540, after the first time was determined to occur within the threshold time period of the second time at block 530, one or more security response actions may be performed. As an example, referring back to the interface of FIG. 4, if an elevated heart rate was detected at block 510, and either sound or movement was detected as the type of security alert at block 520, and these two events were determined to occur within a threshold period of time of each other, the security response action may be to turn on a light, such as a light that is closest to the user or where the sound was detected. After a defined time period, if the user has not provided input to the home automation host system to disable actions being performed, a second action may be taken, such as by outputting sound. Outputting sound may involve the home automation host system turning on a sound system and/or presentation device such that either recorded content or a live television channel is output. The home automation host system may set the volume to a user-defined level. If the home automation host system is incorporated as part of a television receiver, no transmission of data external to the home automation host system may be necessary to activate the television receiver and adjust the volume. If the home automation host system is external to the television receiver, such as an overlay device, either a wired or wireless data transmission may be used to activate the television receiver and adjust the volume to an appropriate level. If stored content is to be output, the user may be permitted to define a particular piece of content or segment of a piece of content to use. These selected segments of content may be selected for having scary or human sounds, such as animal noises or people talking. If a biometric alert or security alert was detected without a corresponding alert of the other type, the type of response performed by the home automation host system may be different from the response performed if both types of alerts were detected within the threshold period of time of each other.

Figure 6:
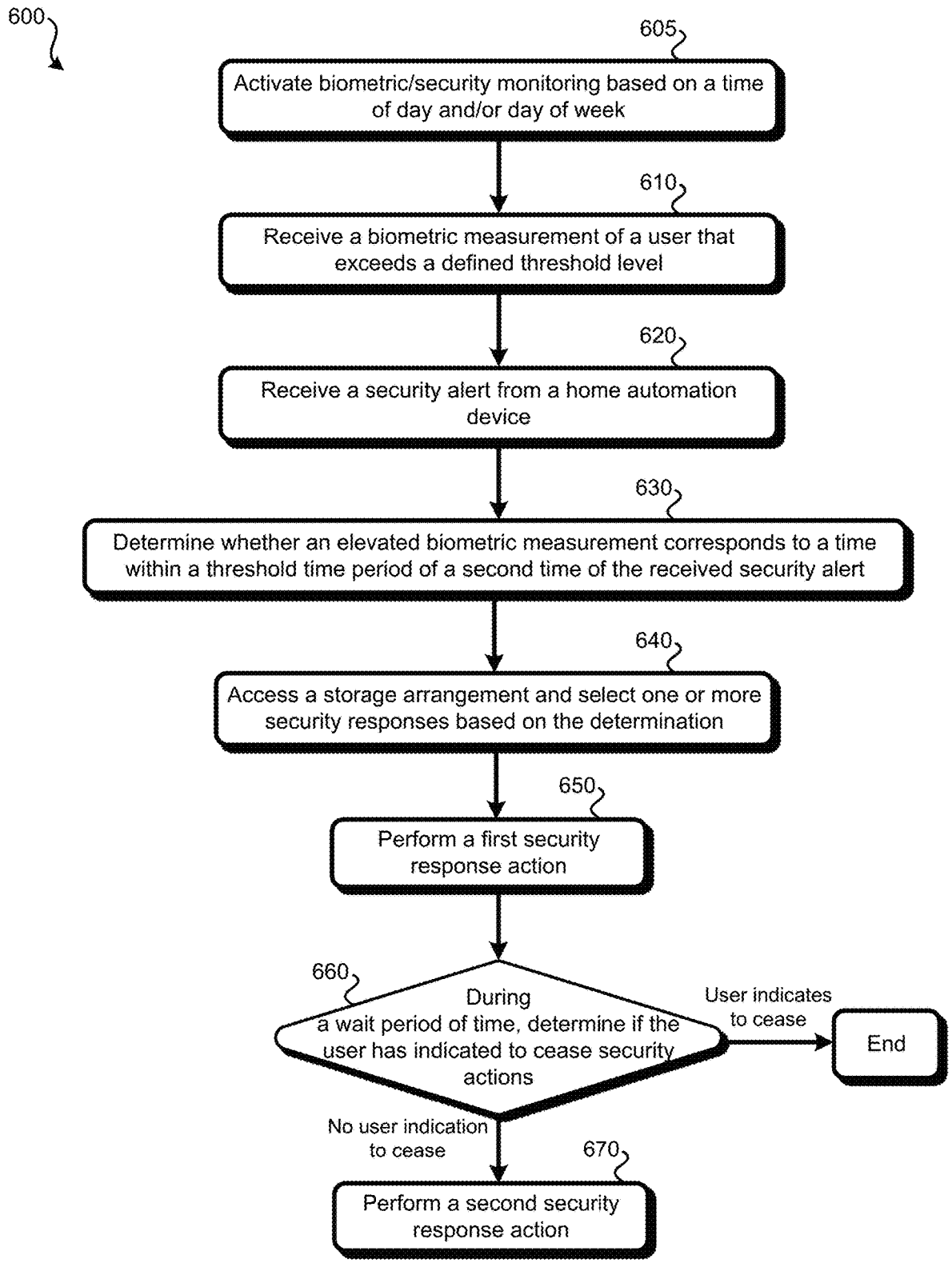
FIG. 6 illustrates another embodiment of a method for handling a potential security situation using a home automation system.

FIG. 6 illustrates an embodiment of a method 600 for handling a potential security situation using a home automation system. Method 600 may be performed using various home automation systems, such as the home automation systems detailed in relation to FIGS. 1-4. Each step of method 600 may be performed by the home automation host system. Method 600 may represent a more detailed embodiment of method 500 of FIG. 5.

At block 605, biometric and/or security monitoring may be activated based on the time of day and/or day of the week. A user may defined specific times of the day and/or days of the week during which the home automation host system is actively monitoring for a biometric alert occurring within a defined time of a security alert. For example, referring to the interface of FIG. 4, a user may set the active times a day and/or days of week via active time period option 431. In some embodiments, the home automation host system may monitor for when biometric and/or security monitoring should occur based on the location (e.g., in bed, on the couch) of the user and/or the user's activity level (e.g., if the user is stationary for an extended time, he is likely asleep).

At block 610, a biometric measurement of the user may be received by the home automation host system. In some embodiments, the home automation host system may determine that the received biometric measurement exceeds a defined threshold level specific to that type of biometric measurement. In other embodiments, rather than the home automation host system performing a comparison between the biometric measurement and the defined threshold level, such an analysis may be performed by the biometric device itself; thus, the received biometric measurement may serve as a biometric alert.

At block 620, a security alert from a home automation device may be received by the home automation host system. In some embodiments, the data received from the home automation device is analyzed by the home automation host system to determine whether a security alert is present. In other embodiments, the home automation device itself analyzes the data and determines that a security alert is present and transmits indication of the security alert to the home automation host system.

At block 630, it is determined whether the biometric measurement of block 610 corresponds to a time within a defined threshold period of time of the security alert of block 620. Therefore, if the biometric measurement is received (or measured) at a first time and the security alert is received (or measured) at a second time, it is determined whether the first time is within a threshold time period of the second time. If it is not, it may be assumed that the biometric measurement of block 610 is unrelated to the security alert of block 620. If the first and second times are within a threshold time period of each other, it may be determined that the biometric measurement of block 610 is related to the security alert of block 620. As a simple example, the threshold time period may be 20 seconds; of course, threshold time periods that are of shorter duration or longer duration are also possible.

At block 640, a storage arrangement may be accessed to determine an appropriate security response based on the biometric measurement of block 610, the security alert of block 620, and determining that the biometric measurement and the security alert occurred within a threshold time period at block 630. Referring to FIG. 2, defined responses database 206 may be accessed from a non-transitory computer readable medium. Referring to the interface of FIG. 4, it can be seen how a user may define particular actions to be taken in response to particular combinations of biometric alerts and security alerts.

At block 650, a first security response action may be performed based on information accessed at block 640. As an example, a first security response action may include action such as: turning on one or more lights, outputting sound via a presentation device or sound system, contacting an emergency contact, recording video, recording sound, or performing some other action that is possible to be performed by one or more home automation devices located within the user's structure.

At block 660, a defined wait period of time (which corresponds to the defined time period between actions option 434) may be monitored by the home automation host system after the first security response action. During this time period, the home automation host system may be monitoring for user input to the home automation host system that disables the security response(s) (e.g., a voice command, user input to the biometric device, user input directly to the home automation host system, etc.). If the user provides such input, method 600 may end and the home automation host system may not perform a second security response action. If the user does not provide user input during the wait period of time, method 600 may proceed to block 670 and a second security response action may be performed. The second response action may typically be more dire than the first security response action (since the user did not disable future security responses at block 660). For instance, a typical second security response action may be an automated call to 911 (or, more generally, an emergency service) or to a defined contact of the user.

Figure 7:
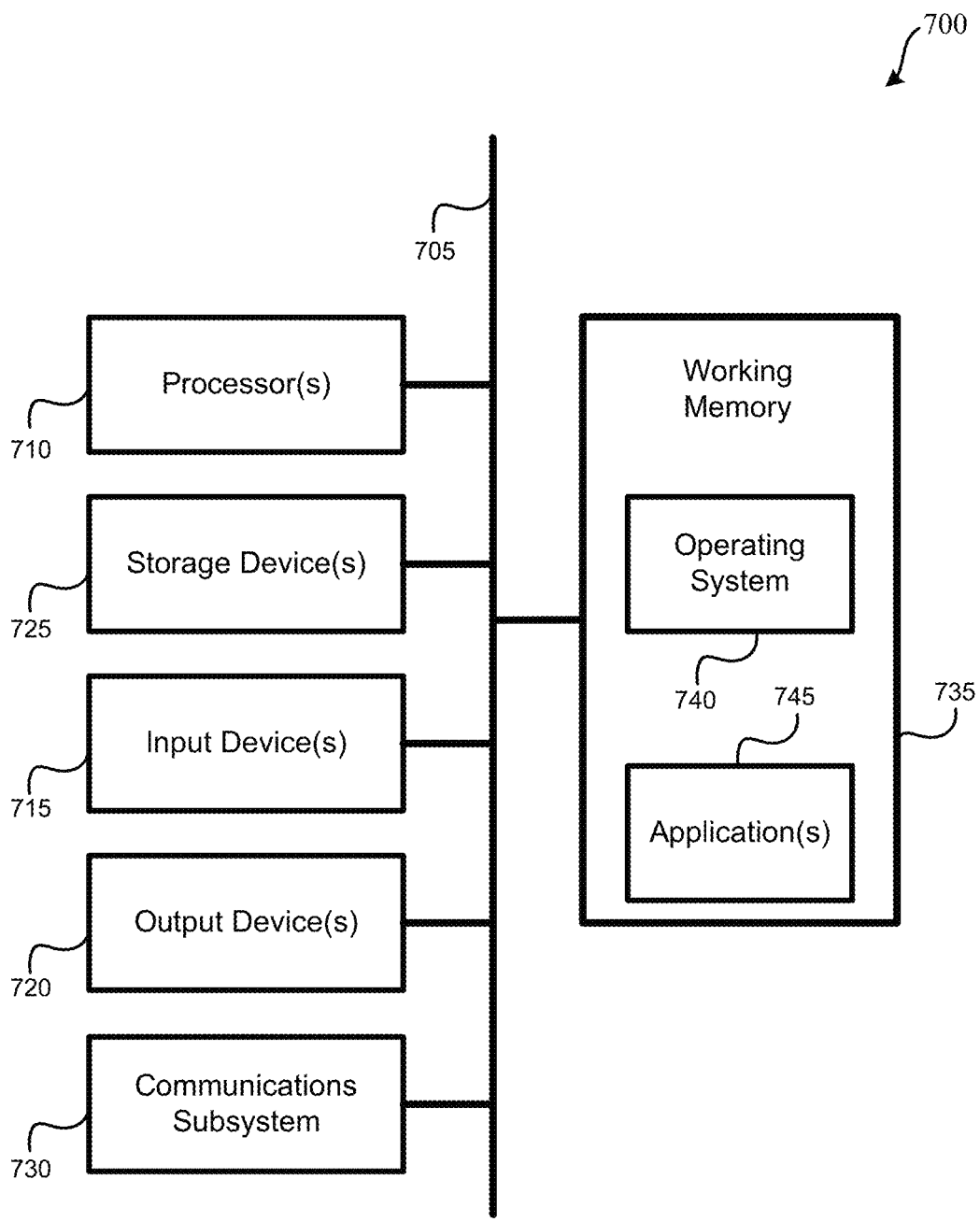
FIG. 7 illustrates an embodiment of a computer system which may be incorporated as part of various computerized devices in a home automation system.

FIG. 7 illustrates an embodiment of a computer system which may be incorporated as part of various computerized devices in a home automation system. A computer system as illustrated in FIG. 7 may be incorporated as part of the previously described home automation host system and, possibly, as any of the home automation devices detailed. FIG. 7 provides a schematic illustration of one embodiment of a computer system 700 that can perform various steps of the methods provided by various embodiments. It should be noted that FIG. 7 is meant only to provide a generalized illustration of various components, any or all of which may be utilized as appropriate. FIG. 7, therefore, broadly illustrates how individual system elements may be implemented in a relatively separated or relatively more integrated manner.

The computer system 700 is shown comprising hardware elements that can be electrically coupled via a bus 705 (or may otherwise be in communication, as appropriate). The hardware elements may include one or more processors 710, including without limitation one or more general-purpose processors and/or one or more special-purpose processors (such as digital signal processing chips, graphics acceleration processors, video decoders, and/or the like); one or more input devices 715, which can include without limitation a mouse, a keyboard, remote control, and/or the like; and one or more output devices 720, which can include without limitation a display device, a printer, and/or the like.

The computer system 700 may further include (and/or be in communication with) one or more non-transitory storage devices 725, which can comprise, without limitation, local and/or network accessible storage, and/or can include, without limitation, a disk drive, a drive array, an optical storage device, a solid-state storage device, such as a random access memory ("RAM"), and/or a read-only memory ("ROM"), which can be programmable, flash-updateable and/or the like. Such storage devices may be configured to implement any appropriate data stores, including without limitation, various file systems, database structures, and/or the like.

The computer system 700 might also include a communications subsystem 730, which can include without limitation a modem, a network card (wireless or wired), an infrared communication device, a wireless communication device, and/or a chipset (such as a Bluetooth™ device, an 802.11 device, a WiFi device, a WiMax device, cellular communication device, etc.), and/or the like. The communications subsystem 730 may permit data to be exchanged with a network (such as the network described below, to name one example), other computer systems, and/or any other devices described herein. In many embodiments, the computer system 700 will further comprise a working memory 735, which can include a RAM or ROM device, as described above.

The computer system 700 also can comprise software elements, shown as being currently located within the working memory 735, including an operating system 740, device drivers, executable libraries, and/or other code, such as one or more application programs 745, which may comprise computer programs provided by various embodiments, and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be stored on a non-transitory computer-readable storage medium, such as the non-transitory storage device(s) 725 described above. In some cases, the storage medium might be incorporated within a computer system, such as computer system 700. In other embodiments, the storage medium might be separate from a computer system (e.g., a removable medium, such as a compact disc), and/or provided in an installation package, such that the storage medium can be used to program, configure, and/or adapt a general purpose computer with the instructions/code stored thereon. These instructions might take the form of executable code, which is executable by the computer system 700 and/or might take the form of source and/or installable code, which, upon compilation and/or installation on the computer system 700 (e.g., using any of a variety of generally available compilers, installation programs, compression/decompression utilities, etc.), then takes the form of executable code.

It will be apparent to those skilled in the art that substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

As mentioned above, in one aspect, some embodiments may employ a computer system (such as the computer system 700) to perform methods in accordance with various embodiments of the invention. According to a set of embodiments, some or all of the procedures of such methods are performed by the computer system 700 in response to processor 710 executing one or more sequences of one or more instructions (which might be incorporated into the operating system 740 and/or other code, such as an application program 745) contained in the working memory 735. Such instructions may be read into the working memory 735 from another computer-readable medium, such as one or more of the non-transitory storage device(s) 725. Merely by way of example, execution of the sequences of instructions contained in the working memory 735 might cause the processor(s) 710 to perform one or more procedures of the methods described herein.

The terms "machine-readable medium," "computer-readable storage medium" and "computer-readable medium," as used herein, refer to any medium that participates in providing data that causes a machine to operate in a specific fashion. These mediums may be non-transitory. In an embodiment implemented using the computer system 700, various computer-readable media might be involved in providing instructions/code to processor(s) 710 for execution and/or might be used to store and/or carry such instructions/code. In many implementations, a computer-readable medium is a physical and/or tangible storage medium. Such a medium may take the form of a non-volatile media or volatile media. Non-volatile media include, for example, optical and/or magnetic disks, such as the non-transitory storage device(s) 725. Volatile media include, without limitation, dynamic memory, such as the working memory 735.

Common forms of physical and/or tangible computer-readable media include, for example, a floppy disk, a flexible disk, hard disk, magnetic tape, or any other magnetic medium, a CD-ROM, any other optical medium, any other physical medium with patterns of marks, a RAM, a PROM, EPROM, a FLASH-EPROM, any other memory chip or cartridge, or any other medium from which a computer can read instructions and/or code.

Various forms of computer-readable media may be involved in carrying one or more sequences of one or more instructions to the processor(s) 710 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer system 700.

The communications subsystem 730 (and/or components thereof) generally will receive signals, and the bus 705 then might carry the signals (and/or the data, instructions, etc. carried by the signals) to the working memory 735, from which the processor(s) 710 retrieves and executes the instructions. The instructions received by the working memory 735 may optionally be stored on a non-transitory storage device 725 either before or after execution by the processor(s) 710.

It should further be understood that the components of computer system 700 can be distributed across a network. For example, some processing may be performed in one location using a first processor while other processing may be performed by another processor remote from the first processor. Other components of computer system 700 may be similarly distributed. As such, computer system 700 may be interpreted as a distributed computing system that performs processing in multiple locations. In some instances, computer system 700 may be interpreted as a single computing device, such as a distinct laptop, desktop computer, or the like, depending on the context.

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of the invention. Also, a number of steps may be undertaken before, during, or after the above elements are considered.

What is claimed is:

1. A method for responding to a security situation, the method comprising:
   receiving, by a home automation host system, a biometric measurement of a user;
   determining, by the home automation host system, that the biometric measurement meets a defined threshold;
   receiving, by the home automation host system, security data from a home automation device in communication with the home automation host system;
   determining, by the home automation host system, the biometric measurement is associated with the security data received from the home automation device; and
   in response to the biometric measurement meeting the defined threshold and the security data received from the home automation device, performing, by the home automation host system, a security response action.

2. The method of claim 1, wherein the security response action comprises presenting, via a display device, a video feed from a camera that captures video corresponding to a location of the security situation.

3. The method of claim 1, wherein the security response action comprises contacting an emergency service.

4. The method of claim 1, wherein the security response action comprises:
   activating a sound system; and
   transmitting an instruction to output sound to the sound system.

5. The method of claim 4, wherein the security response action further comprises:
   transmitting a second instruction to set a defined volume level for outputting sound via the sound system.

6. The method of claim 1, wherein the biometric measurement is a heart rate.

7. The method of claim 1, further comprising:
   providing a questionnaire via a presentation device, wherein the questionnaire presents an option as to how the home automation host system should respond to the security situation if the biometric measurement of the user exceeds a threshold value.

8. The method of claim 1, wherein the security response action comprises:
causing a message to be sent to an external contact.

9. The method of claim 1, wherein the security response action comprises the home automation host system transmitting a message that causes a light to be illuminated.

10. A home automation host system comprising:
one or more processors; and
a memory communicatively coupled with and readable by the one or more processors and having stored therein processor-readable instructions which, when executed by the one or more processors, cause the one or more processors to:
receive a biometric measurement of a user;
determine that the biometric measurement meets a defined threshold;
receive data from a home automation device in communication with the home automation host system;
determine the biometric measurement is associated with the data received from the home automation device; and
perform a security response action in response to the biometric measurement meeting the defined threshold and the data received from the home automation device for a security situation.

11. The home automation host system of claim 10, wherein the processor-readable instructions that, when executed, cause the one or more processors to perform the security response action comprise processor-readable instructions which, when executed, cause the one or more processors to cause a video feed from a camera to be displayed by a display device.

12. The home automation host system of claim 10, wherein the security response action comprises contacting an emergency service.

13. The home automation host system of claim 10, wherein the processor-readable instructions that, when executed, cause the one or more processors to perform the security response action comprise processor-readable instructions which, when executed, cause the one or more processors to:
activate a sound system; and
cause sound to be output.

14. The home automation host system of claim 13, wherein the processor-readable instructions that, when executed, cause the one or more processors to perform the security response action further comprise processor-readable instructions which, when executed, cause the one or more processors to:
set a defined volume level for outputting sound via the sound system.

15. The home automation host system of claim 10, wherein the biometric measurement is a heart rate.

16. The home automation host system of claim 10, wherein the processor-readable instructions, when executed, further cause the one or more processors to:
output a questionnaire via a presentation device, wherein the questionnaire presents an option to the user as to how the home automation host system should respond to the security situation if the biometric measurement of the user exceeds a defined threshold value.

17. The home automation host system of claim 10, wherein the processor-readable instructions that, when executed, cause the one or more processors to perform the security response action comprise processor-readable instructions which, when executed, cause the one or more processors to:
cause a message to be sent to a defined external contact, the defined external contact being defined by the user.

18. The home automation host system of claim 10, wherein the processor-readable instructions that, when executed, cause the one or more processors to perform the security response action comprise processor-readable instructions which, when executed, cause the one or more processors to cause a light to be illuminated.

19. A non-transitory processor-readable medium comprising processor-readable instructions configured to cause one or more processors of a home automation host system to:
receive a biometric measurement of a user;
determine that the biometric measurement meets a defined threshold;
receive data from a home automation device in communication with the home automation host system;
determine the biometric measurement is associated with the data received from the home automation device; and
perform a security response action in response to the biometric measurement meeting the defined threshold and the data received from the home automation device.

20. The non-transitory processor-readable medium of claim 19, wherein the biometric measurement is a heartrate of the user.

* * * * *